US010954205B2

(12) United States Patent
Beato et al.

(10) Patent No.: US 10,954,205 B2
(45) Date of Patent: Mar. 23, 2021

(54) PROCESS FOR OXIDATION OF A LOWER ALKENE AT LOW TEMPERATURES IN AMMONIA-CONTAINING GAS MIXTURES

(71) Applicant: HALDOR TOPSØE A/S, Kgs. Lyngby (DK)

(72) Inventors: Pablo Beato, København S (DK); Ton V. W. Janssens, Bagsværd (DK)

(73) Assignee: HALDOR TOPSØE A/S, Kgs. Lyngby (DK)

( * ) Notice: Subject to any disclaimer, the term of this patent is extended or adjusted under 35 U.S.C. 154(b) by 0 days.

(21) Appl. No.: 16/619,254

(22) PCT Filed: Jun. 7, 2018

(86) PCT No.: PCT/EP2018/064958
§ 371 (c)(1),
(2) Date: Dec. 4, 2019

(87) PCT Pub. No.: WO2018/234045
PCT Pub. Date: Dec. 27, 2018

(65) Prior Publication Data
US 2020/0095216 A1 Mar. 26, 2020

(30) Foreign Application Priority Data

Jun. 23, 2017 (DK) .......................... PA 2017 00375

(51) Int. Cl.
*C07D 301/08* (2006.01)
*C07C 29/48* (2006.01)
*C07C 45/34* (2006.01)

(52) U.S. Cl.
CPC ............ *C07D 301/08* (2013.01); *C07C 29/48* (2013.01); *C07C 45/34* (2013.01)

(58) Field of Classification Search
CPC ........ C07D 301/08; C07C 29/48; C07C 45/34
USPC ....................................... 549/523
See application file for complete search history.

(56) References Cited

U.S. PATENT DOCUMENTS

| 3,965,185 A | 6/1976 | Young |
| 2001/0044557 A1 | 11/2001 | Bhasin et al. |
| 2009/0050535 A1 | 2/2009 | Evans |
| 2011/0152546 A1 | 6/2011 | Senkan et al. |
| 2017/0021337 A1* | 1/2017 | Nagy ..................... B01J 23/686 |

FOREIGN PATENT DOCUMENTS

| CN | 101985016 A | 3/2011 |
| EP | 2980082 A1 | 2/2016 |
| EP | 3090997 A1 | 11/2016 |
| GB | 1373489 A | 11/1974 |
| JP | S53012803 A | 2/1978 |
| WO | 9505896 A1 | 3/1995 |
| WO | 2004078737 A1 | 9/2004 |
| WO | 2011046621 A1 | 4/2011 |
| WO | 2012009052 A1 | 1/2012 |
| WO | 2012141942 A1 | 10/2012 |
| WO | 2015154827 A1 | 10/2015 |
| WO | 2015154828 A1 | 10/2015 |
| WO | 2015154829 A1 | 10/2015 |
| WO | 2016177924 A1 | 11/2016 |
| WO | 2017083338 A1 | 5/2017 |
| WO | 2017083773 A1 | 5/2017 |

OTHER PUBLICATIONS

International Search Report (PCT/ISA/210) and Written Opinion (PCT/ISA/237) dated Jul. 6, 2018, by the European Patent Office as the International Searching Authority for International Application No. PCT/EP2018/064958.
Search Report dated Oct. 23, 2017, by the Danish Patent Office for Application No. PA 2017 00375.
Groothaert, M. H. et al., "Selective Oxidation of Methane by the Bis(i-oxo)dicopper Core Stabilized on ZSM-5 and Mordenite Zeolites" J. Am. Chem. Soc. vol. 127, No. 5, pp. 1394-1395, Jan. 15, 2005).
Smeets, P. J. et al., "Cu based zeolites: A UV-vis study of the active site in the selective methane oxidation at low temperatures" Elsevier, Catal. Today 110, pp. 303-309, (2005).
Alayon, E. M. C. et al., "Reaction Conditions of Methane-to-Methanol Conversion Affect the Structure of Active Copper Sites" ACS Catalysis, vol. 4, No. 16, pp. 16-22, (2014).
Le, H. et al., "Solid-State Ion-Exchanged Cu/Mordenite Catalysts for the Direct Conversion of Methane to Methanol" ACS Catal., vol. 7, pp. 1403-1412, (2017).
Markovits, M. A. C. et al., "Effect of Location and Distribution of Al Sites in ZSM-5 on the Formation of Cu-Oxo Clusters Active for Direct Conversion of Methane to Methanol" Top. Catal., vol. 59, pp. 1554-1563, (2016).
Gao, F. et al. "Understanding ammonia selective catalytic reduction kinetics over Cu/SSZ-13 from motion of the Cu ions" J. Catal. vol. 319, pp. 1-14, (2014).
Janssens, T.V. W. et al., "A Consistent Reaction Scheme for the Selective Catalytic Reduction of Nitrogen Oxides with Ammonia" ACS Catal., vol. 5, pp. 2832-2845, (2015).
Paolucci, C. et al., "Catalysis in a Cage: Condition-Dependent Speciation and Dynamics of Exchanged Cu Cations in SSZ-13 Zeolites" J. Am. Chem. Soc., vol. 138, pp. 6028-6048, (2016).
Shwan, S. et al., "Solid-State Ion-Exchange of Copper into Zeolites Facilitated by Ammonia at Low Temperature" ACS Catal. vol. 5, pp. 16-19, (2015).
Sheppard, T., et. al.,"A low temperature, isothermal gas-phase system vor conversin of methane to methanol voer Cu-ZSM-5", Chem Comm., vol. 50, 2014, pp. 11053-11055.

(Continued)

*Primary Examiner* — Taylor V Oh
(74) *Attorney, Agent, or Firm* — Buchanan Ingersoll & Rooney P.C.

(57) ABSTRACT

In a process for the oxidation of a lower alkene, such as ethylene, over a catalyst containing Cu and one or more zeolite or zeotype materials, the oxidation is conducted in the presence of ammonia in the feed gas at a process temperature below 350° C. The oxidation can be performed in a continuous process.

17 Claims, No Drawings

(56) References Cited

OTHER PUBLICATIONS

Wulfers, M.J., et al.,"Conversin of methane to methanol on copper-containing small-pore zeolites and zeotypes", Chem. Comm., vol. 51, 2015, pp. 4447-4450.
Office Action issued by the U.S. Patent and Trademark Office in the U.S. Appl. No. 16/619,270, dated May 26, 2020, U.S. Patent and Trademark Office, Alexandria, VA. (19 pages).

* cited by examiner

PROCESS FOR OXIDATION OF A LOWER ALKENE AT LOW TEMPERATURES IN AMMONIA-CONTAINING GAS MIXTURES

The present invention relates to a process for oxidation of a lower alkene, such as ethylene or propylene, in ammonia-containing gas mixtures and catalysts for use in the process. The invention is based on the finding that oxygen can be activated by mobile Cu-ammonia complexes formed inside the cavities of a zeolite. The term "lower alkene" refers to an alkene containing from 1 to 5 carbon atoms in the molecule.

Partial oxidation of ethylene ($C_2H_4$) to ethylene oxide ($C_2H_4O$) is industrially catalyzed by silver, and it is an important industrial process with a large production capacity. Due to the global capacity of this process, even slight improvements in the selectivity would have large scale economical benefits. Processes and catalysts for the oxidation of ethylene to ethylene oxide are described e.g. in WO 95/05896 A1, WO 2004/078737 A1, WO 2012/141942 A1 and EP 2 980 082 A1.

The overall reaction comprises three reactions: (1) the selective oxidation of ethylene to ethylene oxide ($C_2H_4 + \frac{1}{2}O_2 \leftrightarrow C_2H_4O$), (2) the unselective oxidation of ethylene to $CO_2$ and $H_2O$ ($C_2H_4 + 3O_2 \rightarrow 2CO_2 + 2H_2O$) and (3) the over-oxidation of ethylene oxide to $CO_2$ and $H_2O$ ($C_2H_4O + 2.5O_2 \rightarrow 2CO_2 + 2H_2O$).

The industrial catalyst consists of silver particles supported on low surface alumina (a-$Al_2O_3$), with the addition of alkali compounds as promoters. During the process, chlorine is added in ppm amounts to the feed stream as a promoter in the form of chlorinated hydrocarbons in order to enhance the ethylene oxide selectivity. Today, the ethylene oxide selectivity of the industrial catalyst lies in the range of 80-90%.

One of the challenges of the current process is the high heat of reaction, which limits the conversion of ethylene to below 10% in order to avoid local overheating and hence sintering of the Ag particles, which ultimately leads to a decrease in activity.

Recently, it has been found that Cu-zeolites are able to oxidize methane directly to methanol at around 200° C. (M. H. Groothaert et al., J. Am. Chem. Soc. 127, 1394 (2005); P. J. Smeets et al., Catal. Today 110, 303 (2005), E. M. C. Alayon et al., ACS Catal. 4, 16 (2014); Le, H. et al., ACS Catal. 7, 1403-1412 (2017); Markovits, M. A. C. et al., Top. Catal. 59, 1554-1563 (2016)), which are very mild conditions for the activation of methane. However, the procedure for the conversion to methanol requires an activation of the Cu-zeolite which comprises exposure of the Cu-zeolite to oxygen at temperatures above 400° C. to activate the oxygen. The current interpretation of this partial oxidation of methane to methanol is that the oxidation reaction requires the formation of dimeric Cu—O species, such as Cu—O—Cu, Cu—O—O—Cu, or Cu—$O_2$—Cu, where the actual oxidation of methane then takes place.

Cu-zeolites are also well known catalysts for the selective catalytic reduction of NOx by ammonia ($NH_3$—SCR), which is the basis for the current technology for reduction of NOx emissions from diesel engines and power plants. The $NH_3$—SCR reaction proceeds according to the equation:

$$4NH_3 + 4NO + O_2 \rightarrow 4N_2 + 6H_2O$$

According to this reaction equation, the $NH_3$—SCR reaction also requires an activation of oxygen. On Cu-zeolites, the $NH_3$—SCR reaction proceeds already around 200-250° C. (Gao, F. et al. J. Catal. 319, 1-14 (2014); Janssens, T. V. W. et al., ACS Catal. 5, 2832-2845 (2015); Paolucci, C. et al. J. Am. Chem. Soc. 138, 6028-6048 (2016)). As can be inferred from the reaction equation, this reaction also requires an activation of oxygen on the Cu-zeolites, which implies that oxygen activation takes place at around 200-250° C. in $NH_3$—SCR.

In $NH_3$—SCR, it has been found that the interaction between $NH_3$ and Cu plays a special role. Cu forms stable complexes with ammonia, such as $Cu(NH_3)_4^{2+}$ and $Cu(NH_3)_2^+$ complexes. The $Cu(NH_3)_2^+$ complex is weakly bound in the zeolite (Janssens, T. V. W. et al., ACS Catal. 5, 2832-2845 (2015); Paolucci, C. et al., J. Am. Chem. Soc. 138, 6028-6048 (2016)), which suggests that this complex is mobile under reaction conditions for $NH_3$—SCR.

Applicant's patent applications WO 2015/154829 A1, WO 2015/154828 A1 and WO 2015/154827 A1 describe methods for the preparation of Cu-zeolite and Cu-zeotype materials by mixing a given zeolite or zeotype material in the $H^+$ or $NH_4^+$ form with CuO or $Cu_2O$ powder, followed by exposure to $NH_3$ or a mixture of $NH_3$ with nitrogen oxides at temperatures below 300° C. The materials prepared in this way show an activity for $NH_3$—SCR that is comparable to or exceeds the activity of materials prepared by conventional ion exchange procedures, which means that solid state ion exchange can take place between Cu oxides and zeolites at temperatures below 300° C. in the presence of ammonia. It has been proposed that the ability of performing ion-exchange at low temperatures is due to the mobility of the $Cu(NH_3)_2^+$ complex (Shwan, S. et al., ACS Catal. 5, 16-19 (2015)). The role of the mobility for the activation of oxygen in $NH_3$—SCR in Cu-zeolites has not been established yet.

The above-mentioned WO 2015/154829 A1 discloses that the efficiency of the solid state ion exchange process decreases at temperatures above 350° C. Following the idea that the solid state ion exchange process is due to the mobility of the $Cu(NH_3)_2^+$ complex, it can be deduced from this result that the $Cu(NH_3)_2^+$ complex is not thermally stable above 350° C. This then leads to a loss of the mobility of the Cu-complex.

US 2009/0050535 describes a process for preparing an olefin oxide by reacting a feed comprising an olefin and oxygen. The process, which is carried out as a continuous process, comprises contacting the feed components with an absorbent comprising copper and an epoxidation catalyst comprising a carrier, which may be based on zeolites. A reaction modifier such as ammonia may be present in the feed. This US document, however, relates to a traditional process, such as an ethylene oxide process, and even though copper is present as an absorber in the reactor, the process is very different from the present process.

More specifically, the present invention is built on the observations that oxidation of ethylene at around 200° C. requires an activation of oxygen on a Cu-zeolite or Cu-zeotype, which probably involves more than one Cu-center, and that the presence of ammonia enhances the mobility of the Cu-centers in a Cu-zeolite or Cu-zeotype.

By substituting silver (15-25% Ag on alumina in the prior art industrial catalyst) by Cu (3-5% in the zeolite), the costs of the catalyst can be reduced by a very large factor.

Thus, the present invention concerns a process for the oxidation of a lower alkene over a catalyst containing Cu and a zeolite or a zeotype material at a process temperature below 350° C., wherein the oxidation is conducted in the presence of ammonia in the feed gas. The presence of ammonia is essential to the oxidation of the alkene on Cu-zeolite or Cu-zeotype materials, even though it does not directly take part in the oxidation of the alkene, and it is not necessarily a part of the reaction product. It is also noted that the process of the invention implies activation of oxygen at temperatures below 350° C., and does not require the oxygen activation above 400° C. as described in Le, H. et al., ACS Catal. 7, 1403-1412 (2017) and Markovits, M. A. C. et al., Top. Catal. 59, 1554-1563 (2016).

A lower alkene is a C1-C5 alkene. The preferred lower alkane is ethylene. Another preferred lower alkene is propylene.

A preferred reaction product is ethylene oxide. Another preferred reaction product is propylene oxide.

Other preferred reaction products are ethylene glycol and acetaldehyde.

A first embodiment of the invention is a process in which a gas mixture comprising oxygen, ammonia and a lower alkene is contacted with a Cu-zeolite material at a temperature below 350° C., resulting in an alkene concentration in the product stream that is lower than the concentration in the inlet stream.

Another embodiment of the invention is a process in which a gas mixture comprising oxygen, ammonia and a lower alkene is contacted with a Cu-zeotype material at a temperature below 350° C., resulting in an alkene concentration in the product stream that is lower than the concentration in the inlet stream.

Another embodiment of the invention is a process in which a gas mixture comprising water, ammonia and lower alkene is contacted with a Cu-zeolite material at a temperature below 350° C., resulting in an alkene concentration in the product stream that is lower than the concentration in the inlet stream.

Another embodiment of the invention is a process in which a gas mixture comprising water, ammonia and lower alkene is contacted with a Cu-zeotype material at a temperature below 350° C., resulting in an alkene concentration in the product stream that is lower than the concentration in the inlet stream.

A further embodiment of the invention is a catalyst containing a mixture of a zeolite or a zeotype in the $H^+$ or $NH_4^+$ form and an oxide of Cu.

Preferably the zeolite structure of the Cu-zeolite catalyst is one or more structures selected from the group consisting of AEI, AFX, CHA, KFI, ERI, GME, LTA, IMF, ITH, MEL, MFI, SZR, TUN, *BEA, BEC, FAU, FER, MOR and LEV. It is especially preferred that the Cu-zeolite catalyst is selected from the group consisting of Cu-CHA, Cu-MOR, Cu-MFI, Cu-BEA, Cu-ZSM-5 and Cu-FER.

According to the present invention, the process feed gas mixture comprises oxygen, ammonia and a lower alkene. Other gaseous compounds, such as nitrogen, water, noble gases and other hydrocarbons, can be present in the feed gas mixture as well.

An advantage of the present invention is that the process can be conducted continuously without any need of re-activation of the Cu-zeolite or Cu-zeotype material.

Another advantage of the present invention is that the process can be conducted isothermally at a process temperature between 150 and 350° C. A preferred embodiment of the invention is a process in which the oxidation is performed at a temperature of 250° C. or lower.

A further embodiment of the invention is that the catalyst for the process comprises a mixture of a metal-free zeolite or zeotype material and an oxide of Cu.

Another embodiment of the invention is a process in which a gas mixture comprising oxygen, ammonia and a lower alkene is contacted with a catalyst containing Cu and one or more zeolite or zeotype materials at a temperature below 350° C., in which the concentration of $NH_3$ is between 1 and 5000 ppmv.

Another embodiment of the invention is a process in which a gas mixture comprising oxygen, ammonia and a lower alkene is contacted with a catalyst containing Cu and one or more zeolite or zeotype materials at a temperature below 350° C., in which the concentration of oxygen is 10 vol % or lower.

Another embodiment of the invention is a process in which a gas mixture comprising water, ammonia and a lower alkene is contacted with a catalyst containing Cu and one or more zeolite or zeotype materials at a temperature below 350° C., in which the concentration of water is 10 vol % or lower.

The invention claimed is:

1. A process for the oxidation of a lower alkene over a catalyst,
    wherein the catalyst consists of (i) Cu or an oxide of Cu and (ii) one or more zeolite or zeotype materials, and
    wherein the oxidation is conducted in the presence of ammonia in the feed gas at a process temperature below 350° C. and the reaction product is ethylene oxide, ethylene glycol, acetaldehyde, or propylene oxide.

2. Process according to claim 1, wherein the catalyst consists of (i) an oxide o Cu and (ii) one or more zeolite or zeotype materials.

3. Process according to claim 1, wherein the zeotype is a silico-alumino phosphate material.

4. Process according to claim 1, in which the oxidation is performed in a continuous process.

5. Process according to claim 1, wherein the lower alkene is ethylene.

6. Process according to claim 1, wherein the reaction product is ethylene oxide.

7. A process for the oxidation of a lower alkene over a catalyst containing Cu and one or more zeolite or zeotype materials, wherein the oxidation is conducted in the presence of ammonia in the feed gas at a process temperature below 350° C. and the reaction product is ethylene glycol.

8. A process for the oxidation of a lower alkene over a catalyst containing Cu and one or more zeolite or zeotype materials, wherein the oxidation is conducted in the presence of ammonia in the feed gas at a process temperature below 350° C. and the reaction product is acetaldehyde.

9. Process according to claim 1, wherein the lower alkene is propylene.

10. Process according to claim 1, wherein the reaction product is propylene oxide.

11. Process according to claim 1, wherein the content of ammonia in the feed gas is between 1 and 5000 ppmv.

12. Process according to claim 1, wherein the content of oxygen in the feed gas is 10 vol % or lower.

13. Process according to claim 1, wherein the content of water in the feed gas is 10 vol % or lower.

14. Process according to claim 1, wherein the process temperature is 250° C. or lower.

15. Process according to claim 1, wherein one or more zeolite or zeotype materials in the catalyst have structures selected from the group consisting of AEI, AFX, CHA, KFI, ERI, GME, LTA, IMF, ITH, MEL, MFI, SZR, TUN, *BEA, BEC, FAU, FER, MOR and LEV.

16. Process according to claim 15, wherein the Cu-zeolite catalyst is selected from the group consisting of Cu-CHA, Cu-MOR, Cu-MFI, Cu-BEA, Cu-ZSM-5 and Cu-FER.

17. Process according to claim 15, wherein the Cu-based catalyst is Cu-CHA.

* * * * *